United States Patent

Deweerdt et al.

[11] 4,400,329
[45] Aug. 23, 1983

[54] PROCESS FOR THE MANUFACTURE OF THIOCHLORFORMATES

[75] Inventors: Julien Deweerdt, Toulouse; Jacques Sala, Portet sur Garonne; Denis Souyri, Toulouse, all of France

[73] Assignee: Societe Nationale des Poudres et Explosifs, Paris, France

[21] Appl. No.: 325,369

[22] Filed: Nov. 27, 1981

[30] Foreign Application Priority Data

Dec. 5, 1980 [FR] France .................................. 80 25819

[51] Int. Cl.³ .......................................... C07C 154/00
[52] U.S. Cl. ................................................. 260/455 B
[58] Field of Search ..................................... 260/455 B

[56] References Cited

U.S. PATENT DOCUMENTS 4,320,070 3/1982 Cook, Jr. et al. ............... 260/455 B Primary Examiner—Henry R. Jiles
Assistant Examiner—Robert C. Whittenbaugh
Attorney, Agent, or Firm—Bucknam and Archer

[57] ABSTRACT

According to the invention, phosgene is reacted with a mercaptan in the presence of a catalyst of the general formula:

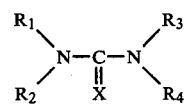

in which X=O or S and in which $R_1$, $R_2$, $R_3$ and $R_4$ are, in particular, aliphatic, cycloaliphatic or aromatic groups or a hydrogen atom. The proportion of catalyst is 0.1 to 10 mol %, relative to the mercaptan, and the reaction is carried out at ambient temperature and at atmospheric pressure. The process, which can be made continuous, results in short residence times and in a high yield and a high purity.

Thiochloroformates are applied essentially as intermediates for the synthesis of herbicidal compounds.

8 Claims, No Drawings

PROCESS FOR THE MANUFACTURE OF THIOCHLORFORMATES

The invention relates to the manufacture of thiochloroformates.

It has long been known that it is possible to obtain thiochloroformates by reacting phosgene with a mercaptan. However, this process, which uses very readily available starting materials, exhibits serious disadvantages. One of these disadvantages is the extremely long reaction time: it is frequently necessary to wait several days before the reaction has reached an acceptable degree of completion. Another disadvantage is the formation of substantial amounts of by-products: these are essentially symmetrical thiocarbonates and disulphides derived therefrom.

Two solutions have been proposed for overcoming these disadvantages in particular. The earlier of these solutions consists in using active charcoal as a reaction catalyst. This solution is described, for example, in French Pat. No. 1,298,704. In fact, it makes it possible considerably to reduce the reaction time, but does not prove entirely satisfactory as regards the reduction in the formation of by-products, because of the existence of unavoidable hot spots in the catalyst charge. Moreover, the nature of the catalyst is the cause of difficulties concerning separation of the reaction product and blocking of the installations.

Recent improvements, described in French Pat. Nos. 2,332,982 and 2,383,172, make it possible, at the expense of greater complexity, to overcome certain disadvantages of the old process without however dispensing with the use of active charcoal.

The second solution has been described in U.S. Pat. No. 3,227,143 and consists in using organic amides, in a variable proportion, as catalysts. In this case, the reaction times are reduced by the same order of magnitude as with active charcoals, but, after a few cycles, sludges are formed which greatly detract from the satisfactory running of the installation, with the result that this process cannot reasonably be employed on an industrial scale.

There is therefore an unsatisfied long-standing need to have available catalysts which are efficient but do not exhibit the disadvantages mentioned above.

The Applicant Company has now found a process for the manufacture of thiochloroformates which uses such catalysts.

The process according to the invention is a process for the manufacture of thiochloroformates by reacting phosgene with a mercaptan in the presence of a catalyst, characterised in that a substituted urea or the reaction product of a urea of this type with phosgene is used as the catalyst.

Ureas which are suitable within the scope of the invention are, in particular, those of the general formula:

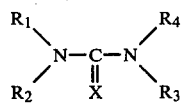

(1)

in which $X=O$ or $S$ and in which $R_1$, $R_2$, $R_3$ and $R_4$ are linear or branched $C_1$ to $C_{18}$, preferably $C_1$ to $C_8$, alkyl radicals, $C_6$ to $C_9$ aryl radicals, $C_7$ to $C_{10}$ alkaryl radicals, $C_7$ to $C_{10}$ aralkyl radicals, $C_2$ to $C_5$ alkenyl radicals or hydrogen atoms, it being possible for $R_1$, $R_2$, $R_3$ and $R_4$ to be all different or all similar, but not all hydrogen atoms, or alternatively $R_1$ and $R_2$ are joined to one another to form a polymethylene chain containing from 4 to 8 members, $R_3$ and $R_4$ having one of the meanings mentioned above or also forming with one another a polymethylene chain containing from 4 to 8 members.

According to a particularly preferred variant of the invention, at least two of the radicals $R_1$, $R_2$, $R_3$ or $R_4$ are linear or branched $C_1$ to $C_8$ alkyl groups.

Particularly preferred ureas which may be mentioned are tetraethylurea, tetrapropylurea, tetrabutylurea, tetraoctylurea, tetraphenylurea, N,N,N'-tributylurea, N,N'-dibutylurea, N,N-diphenylurea, N,N-dibenzylurea, tetra-(p-tolyl)-urea, N,N'-di-(p-tolyl)-urea, N,N'-dimethylurea, N',N'-diethylurea, N,N-diethyl-N',N'-dipropylurea, N,N'-diisopropylurea, N,N-dimethyl-N'-butylurea, N,N'-diisobutylurea, N-propyl-N'-t-butylurea, N,N'-diisohexylurea, N,N'-ditetradecylurea, tetramethylthiourea, tetraethylthiourea, tetrabutylthiourea, N-propyl-N'-isopropylurea, N,N-dimethyl-N'-butylurea, tetraphenylthiourea and dihexamethyleneurea, and also the reaction products of these ureas with phosgene.

The proportion of catalyst which can be used according to the present invention is generally between 0.1 and 10 mol % and preferably between 0.5 and 5 mol %, relative to the mercaptan. This proportion is chosen to be low if the presence of the catalyst in the final product does not seem to be troublesome, for example between 0.5 and 2 mol %. It can be chosen to be higher if the reaction is carried out in a solvent. Furthermore, another factor in the selection of the catalyst and its concentration is the ease with which it can be separated from the reaction mixture, for example by distillation; in this case, the chosen catalyst according to the invention is one having a boiling point which is considerably different from that of the thiochloroformate formed.

The process according to the invention can be carried out batchwise or continuously. The reaction can be carried out in the absence of solvent or in the presence of a solvent which is inert towards phosgene, and this can be, for example, an aromatic solvent such as chlorobenzene, toluene or a xylene, a chlorinated aliphatic solvent such as methylene chloride, or the reaction product itself, in particular in the case, also envisaged according to the invention, of a reaction carried out in a loop reactor. These solvents are chosen according to their ability to dissolve both the mercaptan and the phosgene, that part of the latter which is dissolved in the medium apparently being the part which participates most in the reaction.

The mercaptans to which the present invention applies are those of the general formula RSH, in which R is a linear or branched, preferably $C_1$ to $C_{10}$ alkyl group, a $C_2$ to $C_8$ alkenyl grpup such as an allyl group, a $C_5$ to $C_{12}$ cycloalkyl or cycloalkyl-methyl group, a $C_6$ to $C_{10}$ aromatic group such as a phenyl, chlorophenyl, bromophenyl or benzyl group, or a substituted alkyl group which does not hinder the reaction of the phosgene with the mercaptan, such as the 2-chloropropyl group. The process according to the invention makes it possible, in general, to obtain the thiochloroformates which lead to the thiocarbamates forming part of a large number of herbicidal compositions.

In the process according to the invention, the reaction is carried out at a temperature close to ambient temperature, namely at between −10° and +70° C. and preferably between 5° and 50° C.

In general, it is preferable to avoid carrying out the reaction in the presence of too large an excess of mercaptan, because of the high efficiency of the catalyst; in fact, in the presence of such an excess, the thiochloroformate already formed could react with the unreacted mercaptan, and thiocarbonates and disulphides could be formed. Consequently, it is preferred to form an initial charge of thiochloroformate into which the phosgene and the mercaptan are introduced, preferably simultaneously. An excess of phosgene, which dissolves readily in the thiochloroformate, is not a disadvantage. On the contrary, it is advantageous to favour this excess and this advantage is retained by introducing the phosgene in finely divided form, for example using an injector coupled to means for cooling the reaction medium. In particular in a continuous process, when the equilibrium state has been reached, a 0.5 to 10 mol % excess of phosgene, relative to the mercaptan, proves satisfactory.

Although it is not necessary to carry out the reaction under an inert atmosphere, it is advantageous to carry it out at a pressure above normal pressure, for example ranging from 1 to 10 atmospheres. However, as the catalysts according to the invention already lead to very satisfactory results at atmospheric pressure, it is not generally necessary to resort to this measure, which generates some stresses on the equipment.

As the actual reaction is preferably carried out in a stirred medium, which is effected using a stirred reactor or an injector, for example in a reactor operating as a loop and permitting continuous manufacture, it is rarely necessary to make provision, in a manner known to those skilled in the art, for aging of the reaction medium in an auxiliary reactor which may or may not be fitted with means making it possible to avoid back-mixing.

Depending on the operating conditions, the reaction time is about 1 to 10 hours. The yield obtained at the end of the reaction is generally more than 90% and of the order of 97 to 99%.

The purity of the product obtained is greater than 97% by weight and generally of the order of 98%. Thus, for the majority of applications of thiochloroformates, it is possible to leave the catalyst in the final product without reducing the reactivity of the product and whilst at the same time preserving a satisfactory purity.

Taking account of the fact that only slight advances have been recorded for decades in the field of the manufacture of thiochloroformates, the advantages provided by the present invention will be appreciated all the more, these advantages being a reduction in the severity of the operating conditions (low temperatures, normal pressure), a shortening of the reaction times and an improvement in the yields and the purity, the absence of sludge formation and no observable loss in activity of the catalyst after several recycling operations.

These advantages will be better appreciated and the invention will be understood more clearly with the aid of the following non-limiting examples.

EXAMPLE 1

103 g of octyl thiochloroformate and 42 g of tetrabutylurea were placed in a 1 liter reactor fitted with a stirring device, a device for introducing phosgene, a cooling device and efficient condensers.

30 g of phosgene were introduced into the reactor first and 330 g of phosgene and 438 g of octylmercaptan were then introduced simultaneously in the course of 2 hours, whilst stirring and at the same time maintaining a temperature of the order of 18° C. The amount of catalyst, relative to the thiol, was therefore 5 mol %.

When the introduction had ended, the mixture was kept at the same temperature of 18° C. for one hour, after which the product was degassed under the combined action of a vacuum and bubbled nitrogen.

The product obtained had a boiling point of 105° C. (under 2 mm Hg) and a purity of 99% by gas phase chromatography.

666 g of octyl thiochloroformate were obtained, that is to say a yield of 90%.

EXAMPLE 2

1 kg of octyl thiochloroformate originating from a previous manufacturing operation was placed in a 10 liter reactor fitted with a stirrer and efficient condensing systems, a temperature-measuring device and a device for introducing phosgene.

41 g of tetrabutylurea (that is to say 0.144 mol) and 0.9 kg of phosgene were then introduced successively into the stirred reactor.

3 kg of octylmercaptan (20.5 mols) and 1.35 kg of phosgene were then introduced simultaneously into the reactor, still being stirred, in the course of 2 hours, the temperature being kept at about 30° C.

As soon as the introduction had ended, the reaction mixture was kept at 30° C. for one hour, after which it was degassed as in Example 1.

5.3 kg of a crude reaction mixture containing:
98.2% of octyl thiochloroformate,
0.8% of tetrabutylurea,
0.6% of octyl disulphide and
0.4% of octyl dithiocarbonate, were obtained.

The yield of the operation is of the order of 98%.

EXAMPLE 3

The process described in Example 2 was carried out in a stirred 20 liter reactor, but without introducing any reaction product from a previous manufacturing operation, 277 g of tetrabutylurea and 1 kg of phosgene (that is to say 10.1 mols) being introduced into the reactor first.

6.055 kg of ethylmercaptan (that is to say 97.6 mols) and 9.6 kg of phosgene (that is to say 97 mols) were then introduced, a temperature of 20° C. being maintained.

When the introduction had ended, the mixture was kept at this temperature for 3 hours. The product obtained was degassed and then distilled; it had a boiling point of 50° C. under 31 mm of mercury. 10.9 kg of ethyl thiochloroformate were collected, that is to say a yield of 90%.

We claim:

1. Process for the manufacture of thiochloroformates by reacting phosgene with a mercaptan in the presence of a catalyst, wherein a substituted urea or the reaction product of a substituted urea with phosgene is used as the catalyst and the urea has the formula

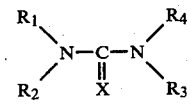

in which X=O or S and in which $R_1$, $R_2$, $R_3$ and $R_4$ are linear or branched $C_1$ to $C_{18}$ alkyl, $C_6$ to $C_9$ aryl, $C_7$ to $C_{10}$ alkaryl, $C_7$ to $C_{10}$ aralkyl, $C_2$ to $C_5$ alkenyl or hydrogen atoms, $R_1$, $R_2$, $R_3$ and $R_4$ being all different or all the same at least one of $R_1$, $R_2$, $R_3$ and $R_4$ being other than hydrogen or alternatively $R_1$ and $R_2$ are joined to one another to form a polymethylene chain containing from 4 to 8 members, or $R_3$ and $R_4$ also forming with one another a polymethylene chain containing from 4 to 8 members.

2. Process according to claim 1, wherein the urea is tetrabutylurea.

3. Process according to claim 1 wherein the proportion of catalyst is between 0.1 and 10 mol % and preferably between 0.5 and 5 mol %, relative to the mercaptan.

4. Process according to claim 1, wherein the reaction is carried out in the presence of a solvent which is inert towards phosgene.

5. Process according to claim 4, wherein the solvent is the reaction product itself.

6. Process according to claim 1, wherein the reaction is carried out at a temperature close to ambient temperature, namely at between −10° and +70° C. and preferably between 5° and 50° C.

7. Process according to claim 1, wherein the process is continuous.

8. Process according to claim 7, wherein when the equilibrium state has been reached, a 0.5 to 10 mol % excess of phosgene is used, relative to the mercaptan.

* * * * *